United States Patent
Clements et al.

(10) Patent No.: US 6,921,385 B2
(45) Date of Patent: Jul. 26, 2005

(54) APPARATUS FOR DELIVERY OF FLUID TO OPTHALMIC SURGICAL HANDPIECE

(75) Inventors: Don A. Clements, Cleburne, TX (US); Lawrence W. Darnell, Cypress, TX (US); Ramon C. Dimalanta, Rancho Santa Margarita, CA (US); Sean C. Madden, Mission Viejo, CA (US); Glenn R. Sussman, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 161 days.

(21) Appl. No.: 10/212,351

(22) Filed: Aug. 5, 2002

(65) Prior Publication Data

US 2004/0024412 A1 Feb. 5, 2004

(51) Int. Cl.⁷ .......................... A61M 37/00; A61M 1/00; A61B 17/20
(52) U.S. Cl. .............................. 604/141; 604/22; 604/27
(58) Field of Search .............................. 604/19, 22, 27, 604/48, 93.01, 131, 132, 140, 141, 147, 148, 151, 153, 244, 246, 256, 257, 403, 408, 410, 415; 606/107, 131, 159; 222/92, 94, 95, 206, 325

(56) References Cited

U.S. PATENT DOCUMENTS

| | | | |
|---|---|---|---|
| 2,678,764 A | 5/1954 | Carlson | |
| 2,766,907 A | 10/1956 | Wallace | |
| 3,507,278 A | * 4/1970 | Werding | ..................... 604/141 |
| 3,589,363 A | 6/1971 | Banko et al. | |
| 3,595,232 A | 7/1971 | Leibinsohn | |
| 3,690,318 A | * 9/1972 | Gorsuch | ..................... 604/141 |
| 3,780,732 A | 12/1973 | Leibinsoh | |
| 3,838,794 A | 10/1974 | Cogley et al. | |
| 3,940,001 A | 2/1976 | Haefner et al. | |

(Continued)

FOREIGN PATENT DOCUMENTS

| | | |
|---|---|---|
| EP | 0 182 094 A2 | 10/1985 |
| EP | 0 355 943 | 2/1990 |
| WO | WO 95/28190 | 10/1995 |
| WO | WO 01/30286 | 5/2001 |

Primary Examiner—Michael J. Hayes
(74) Attorney, Agent, or Firm—W. David Lee

(57) ABSTRACT

An apparatus for delivery of a surgical fluid to a surgical handpiece is disclosed. The apparatus generally includes a container and an adapter receiving one end of the container. The container holds the surgical fluid to be delivered to the handpiece. The adapter is for removably engaging a receptacle in a surgical console and for fluidly coupling with a source of pressurized fluid in a surgical console.

23 Claims, 16 Drawing Sheets

U.S. PATENT DOCUMENTS

| | | | |
|---|---|---|---|
| 3,949,753 A | 4/1976 | Dockhorn | |
| 4,008,830 A | 2/1977 | Meshberg | |
| 4,090,514 A | 5/1978 | Hinck et al. | |
| 4,223,676 A | 9/1980 | Wuchinich et al. | |
| 4,246,902 A | 1/1981 | Martinez | |
| 4,270,533 A | 6/1981 | Andreas | |
| 4,301,802 A | 11/1981 | Poler | |
| 4,330,066 A | 5/1982 | Berliner | |
| 4,337,769 A | 7/1982 | Olson | |
| 4,379,453 A | 4/1983 | Baron | |
| 4,396,382 A | 8/1983 | Goldhaber | |
| 4,493,694 A | 1/1985 | Wuchinich | |
| 4,507,116 A | 3/1985 | Leibinsohn | |
| 4,515,583 A | 5/1985 | Sorich et al. | |
| 4,589,415 A | 5/1986 | Haaga | |
| 4,609,368 A | 9/1986 | Dotson | |
| 4,626,243 A | 12/1986 | Singh et al. | |
| 4,821,896 A | 4/1989 | Cheng | |
| 4,869,715 A | 9/1989 | Sherburne | |
| 4,892,230 A | 1/1990 | Lynn, Jr. | |
| 4,913,698 A * | 4/1990 | Ito et al. | 604/22 |
| 4,922,902 A | 5/1990 | Wuchinich et al. | |
| 4,976,707 A | 12/1990 | Bodicky et al. | |
| 4,989,583 A | 2/1991 | Hood | |
| 5,013,303 A | 5/1991 | Tamari et al. | |
| 5,154,694 A | 10/1992 | Kelman | |
| 5,163,909 A * | 11/1992 | Stewart | 604/140 |
| 5,207,638 A | 5/1993 | Choksi et al. | |
| 5,312,018 A | 5/1994 | Evezich | |
| 5,359,996 A | 11/1994 | Hood | |
| 5,370,609 A * | 12/1994 | Drasler et al. | 604/22 |
| 5,403,276 A | 4/1995 | Schechter et al. | |
| 5,431,627 A | 7/1995 | Pastrone et al. | |
| 5,435,452 A | 7/1995 | Nishigami et al. | |
| 5,436,418 A | 7/1995 | Tamehira | |
| 5,454,486 A | 10/1995 | Mack et al. | |
| 5,497,912 A | 3/1996 | Hoback et al. | |
| 5,505,708 A | 4/1996 | Atkinson | |
| 5,513,761 A | 5/1996 | Kobayashi et al. | |
| 5,531,697 A | 7/1996 | Olsen et al. | |
| 5,616,120 A | 4/1997 | Andrew et al. | |
| 5,620,414 A * | 4/1997 | Campbell, Jr. | 604/22 |
| 5,693,040 A | 12/1997 | Prior | |
| 5,738,657 A | 4/1998 | Bryant et al. | |
| 5,792,133 A | 8/1998 | Rochat | |
| 5,810,202 A | 9/1998 | Hoback et al. | |
| 5,885,243 A | 3/1999 | Capetan et al. | |
| 5,899,674 A | 5/1999 | Jung et al. | |
| 6,036,458 A | 3/2000 | Cole et al. | |
| 6,059,544 A | 5/2000 | Jung et al. | |
| 6,083,450 A | 7/2000 | Safian | |
| 6,135,989 A | 10/2000 | Atad et al. | |
| 6,206,848 B1 | 3/2001 | Sussman et al. | |
| 6,276,567 B1 * | 8/2001 | Diaz et al. | 222/81 |
| 6,340,355 B1 | 1/2002 | Barrett | |
| 6,363,932 B1 | 4/2002 | Forchione et al. | |

\* cited by examiner

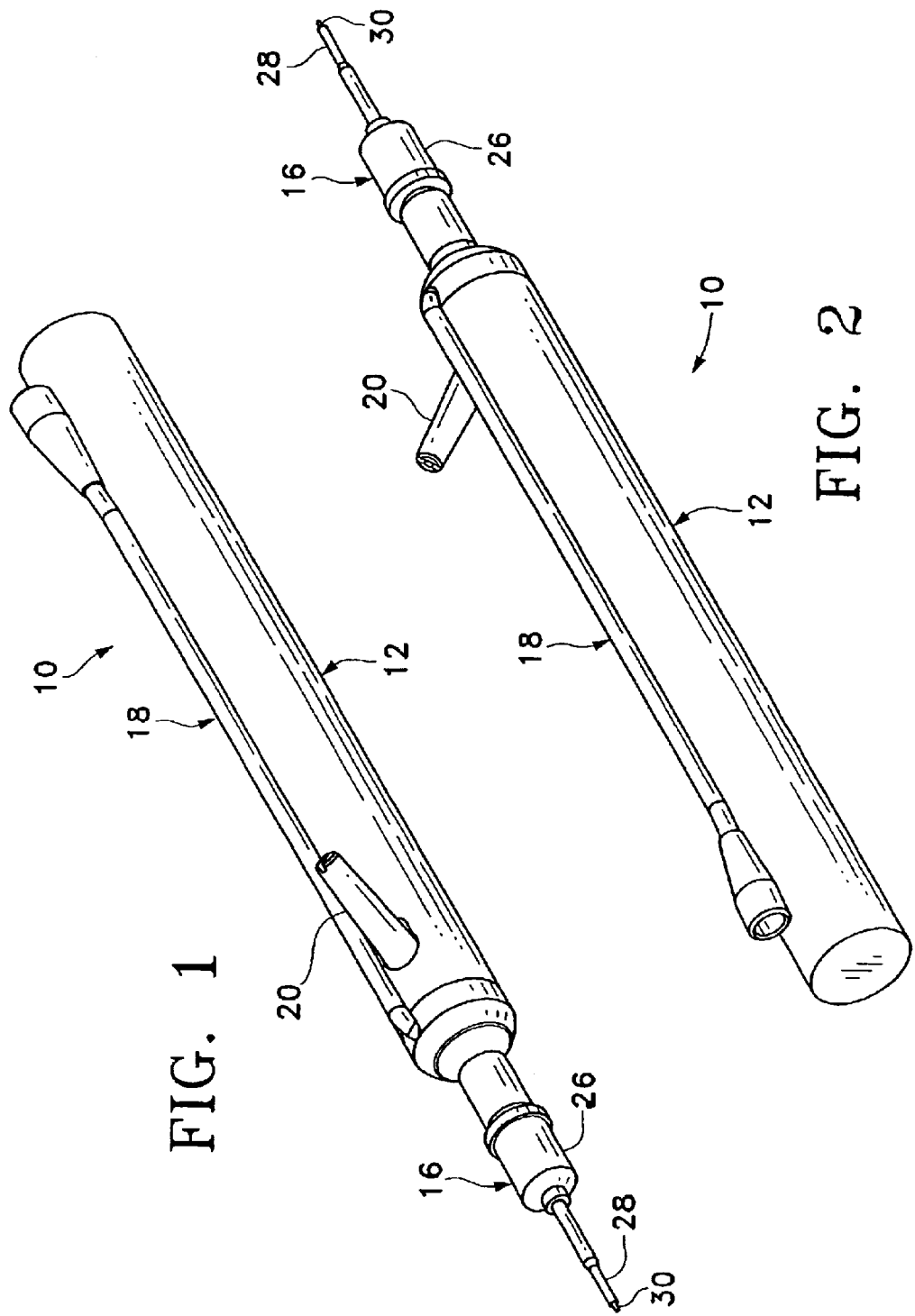

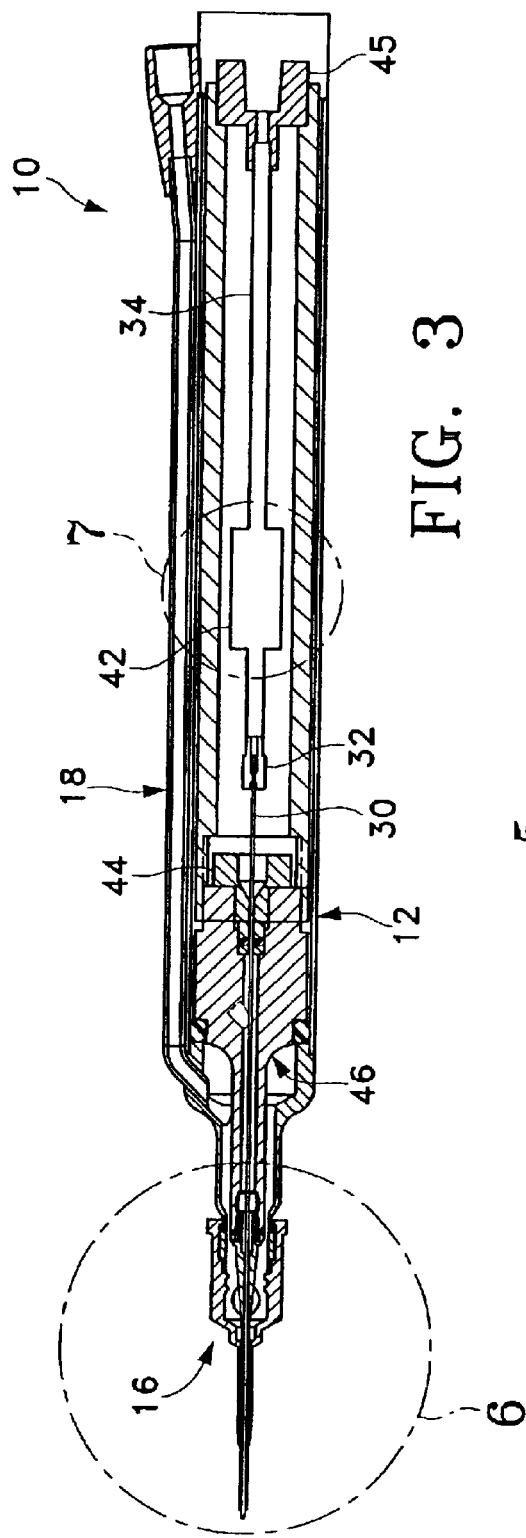
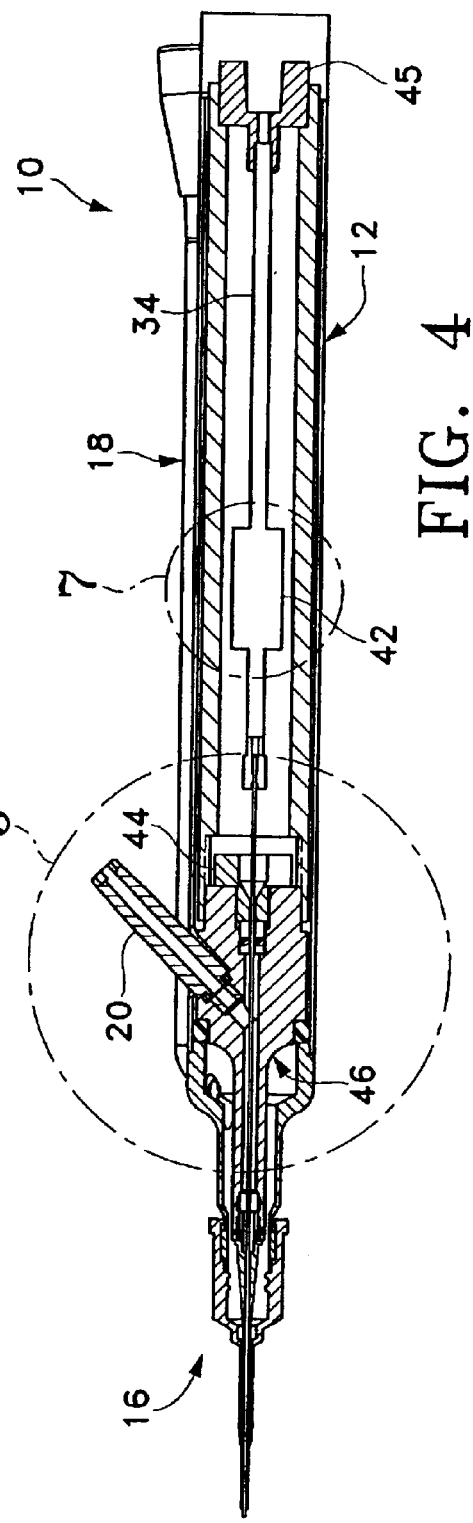

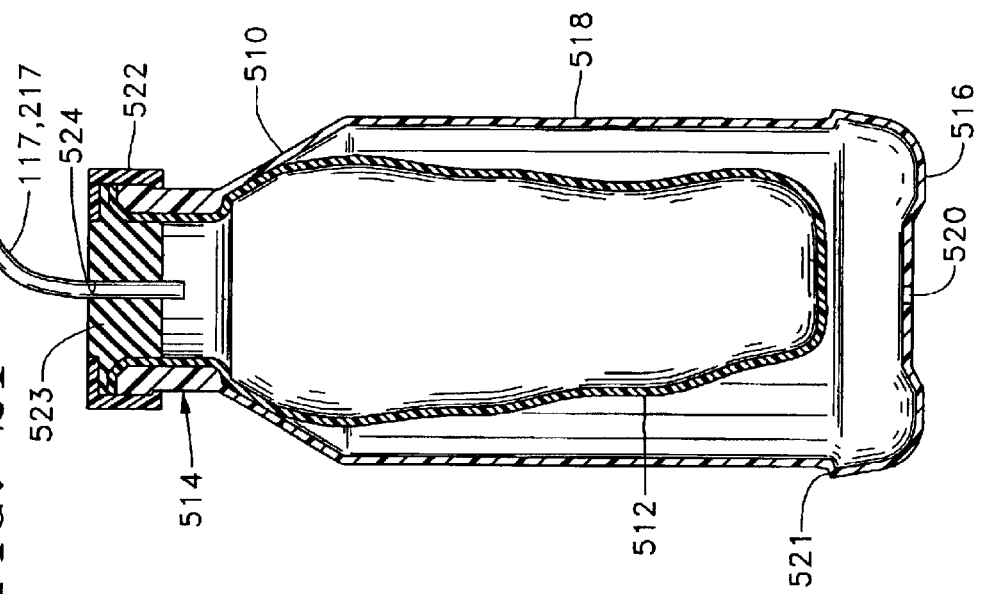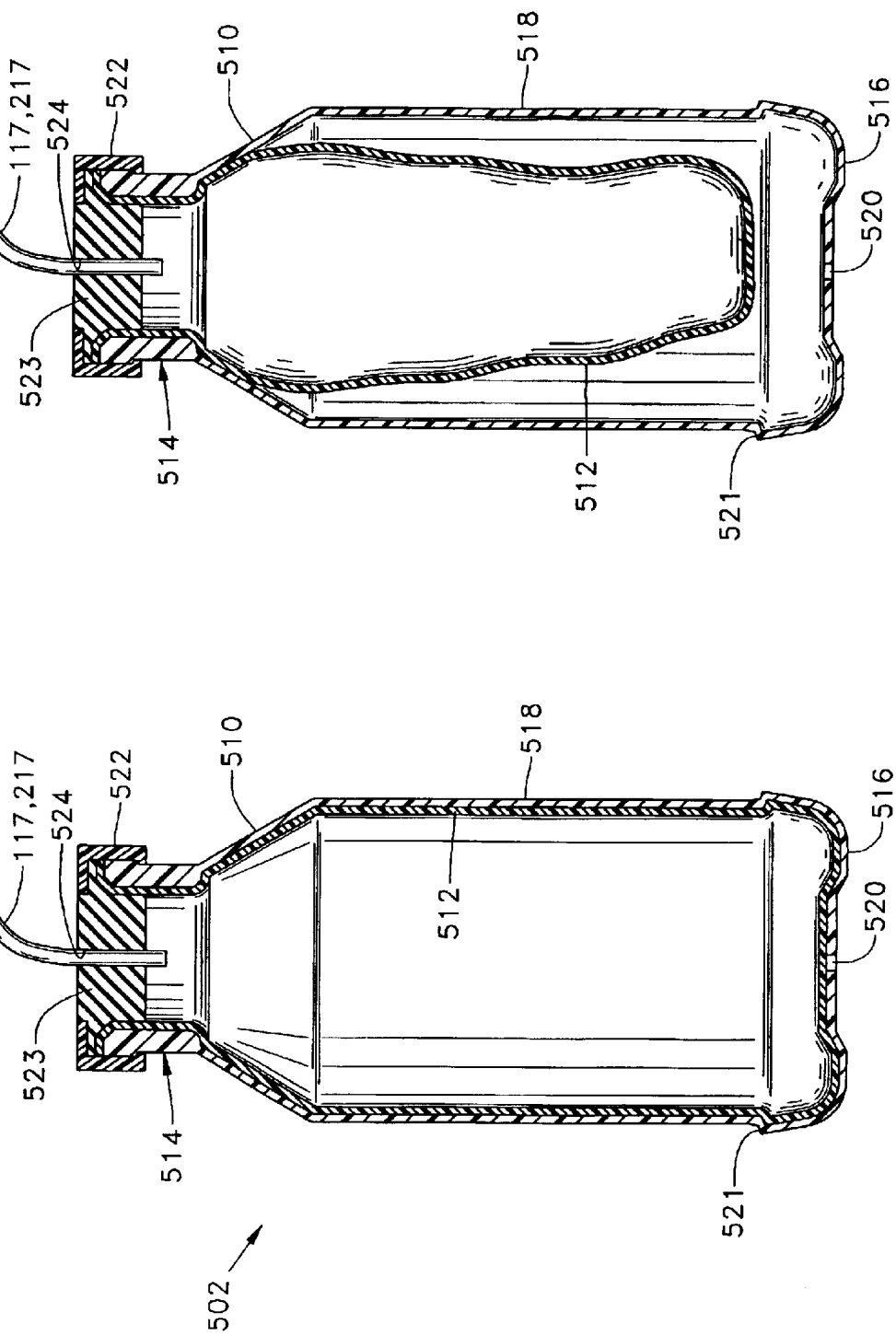

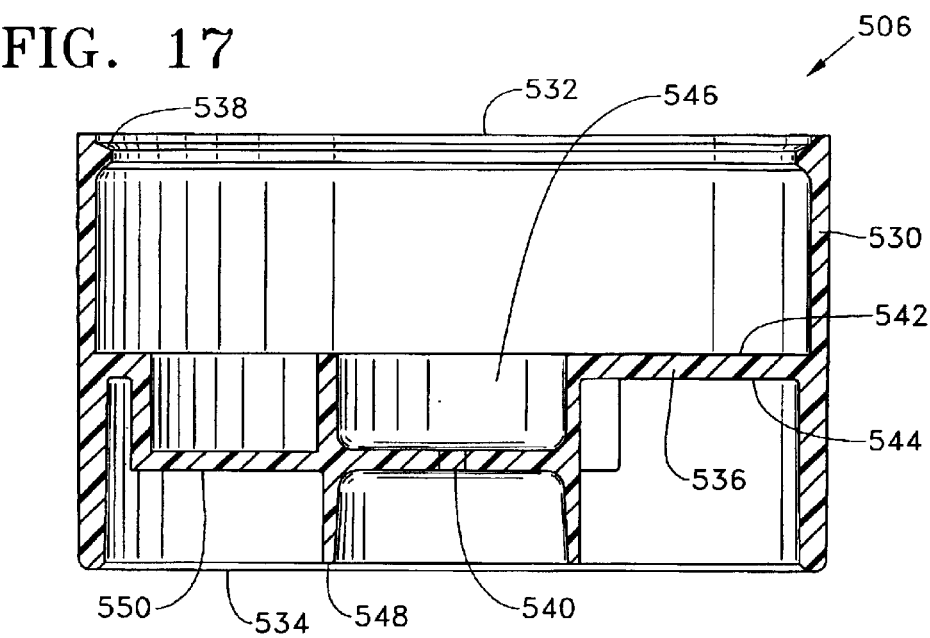
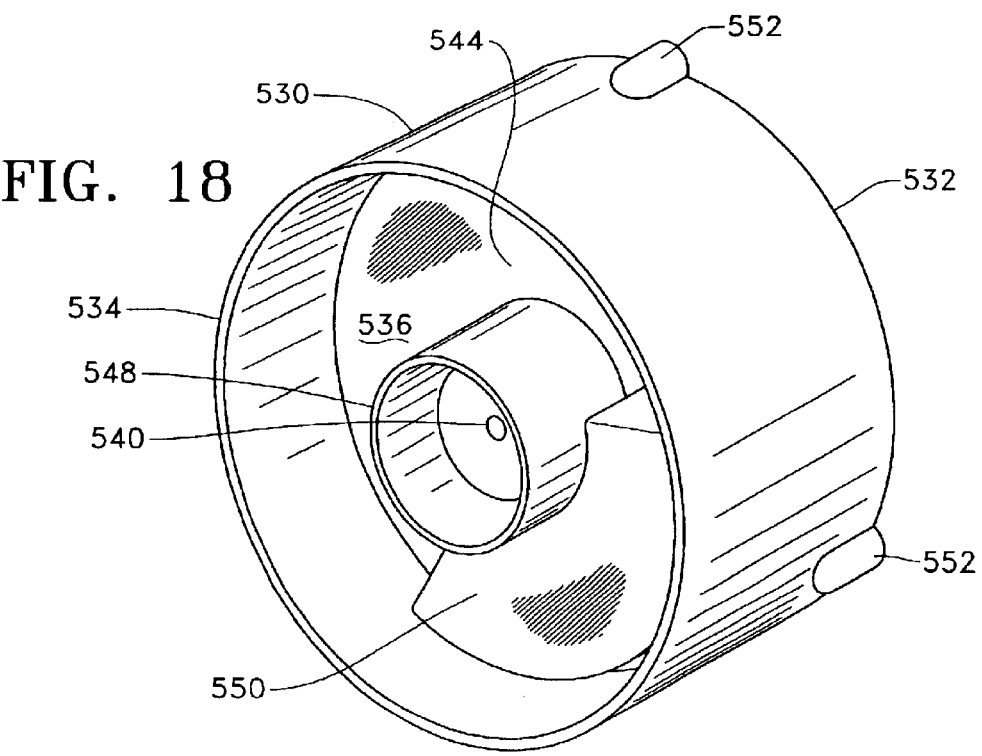

APPARATUS FOR DELIVERY OF FLUID TO OPTHALMIC SURGICAL HANDPIECE

FIELD OF THE INVENTION

This invention relates generally to ophthalmic surgery and more particularly to the liquefracture technique of cataract surgery. The invention also generally pertains to apparatus for the delivery of surgical fluids to ophthalmic microsurgical systems and more particularly to such apparatus for use with a liquefracture handpiece.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, an irrigating sleeve, and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores, and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted concurrently with the injection of the heated solution and the injection of a relatively cool solution, thereby quickly cooling and removing the heated solution. This technique is more fully described in U.S. Pat. No. 5,616,120 (Andrew, et al.), the entire content of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

U.S. Pat. No. 5,885,243 (Capetan, et al.) discloses a handpiece having a separate pumping mechanism and resistive heating element. Such a structure adds unnecessary complexity to the handpiece.

U.S. Pat. No. 6,206,848 (Sussman et al.), which is incorporated in its entirety by this reference, discloses liquefracture handpieces. In the liquefracture technique of cataract removal, the cataractous lens is liquefied or emulsified by repetitive pulses of a surgical fluid that are discharged from the handpiece. The liquefied lens may then be aspirated from the eye. Since the surgical fluid is actually used to liquefy the cataractous lens, a consistent, pressurized source of surgical fluid is important to the success of the liquefracture technique. In addition, different surgical fluids may be advantageous for the removal of different hardness of cataracts or for various patient conditions.

Therefore, a need exists for a simple and reliable apparatus and method of delivering a surgical fluid used to perform the liquefracture technique.

SUMMARY OF THE INVENTION

The present invention is directed to an apparatus for delivery of a surgical fluid to a surgical handpiece. The apparatus generally includes a container and an adapter receiving one end of the container. The container has first and second portions. The first portion is made from a deformable material and has a closed end, an open end, an outer surface, and a first volume for receiving a surgical fluid for delivery to the surgical handpiece. The second portion is made from a material more rigid than the deformable material and has a first end, a second end, an outer surface, an inner surface, and a second volume receiving the first portion. The first end has an outlet for delivery of the surgical fluid. The second end has an aperture for receiving a pressurized fluid between the outer surface of the first portion and the inner surface of the second portion. The adapter has an outer wall, a first open end, a second open end, and a transverse wall coupled to the outer wall with first and second sides. The first end of the adapter receives the second end of the second portion. The second side of the transverse wall has an area for removably engaging a source of the pressurized fluid so that the source of the pressurized fluid is in fluid communication with the aperture.

BRIEF DESCRIPTION OF THE DRAWINGS

For a more complete understanding of the present invention, and for further objects and advantages thereof, reference is made to the following description taken in conjunction with the accompanying drawings in which:

FIG. 1 is a front, upper, left perspective view of a first preferred embodiment of the handpiece of the present invention.

FIG. 2 is a rear, upper, right perspective view of the handpiece of FIG. 1.

FIG. 3 is a cross-sectional view of the handpiece of FIG. 1 taken along a plane passing through the irrigation channel.

FIG. 4 is a cross-sectional view of the handpiece of FIG. 1 taken along a plane passing through the aspiration channel.

FIG. 16 is longitudinal, sectional view of the preferred embodiment of the container of the apparatus of FIG. 15.

FIG. 17 is a longitudinal, sectional view of the preferred embodiment of the adapter of the apparatus of FIG. 15 taken along a plane passing through a raised surface of a transverse wall of the adapter.

FIG. 18 is a rear, right perspective view of the adapter of the apparatus of FIG. 15.

FIG. 21 is a longitudinal, sectional view of the container of the apparatus of FIG. 15 during the discharge of surgical fluid from the container.

DETAILED DESCRIPTION OF THE PREFERRED EMBODIMENTS

The preferred embodiments of the present invention and their advantages are best understood by referring to FIGS. 1–21 of the drawings, like numerals being used for like and corresponding parts of the various drawings.

Figure 6:
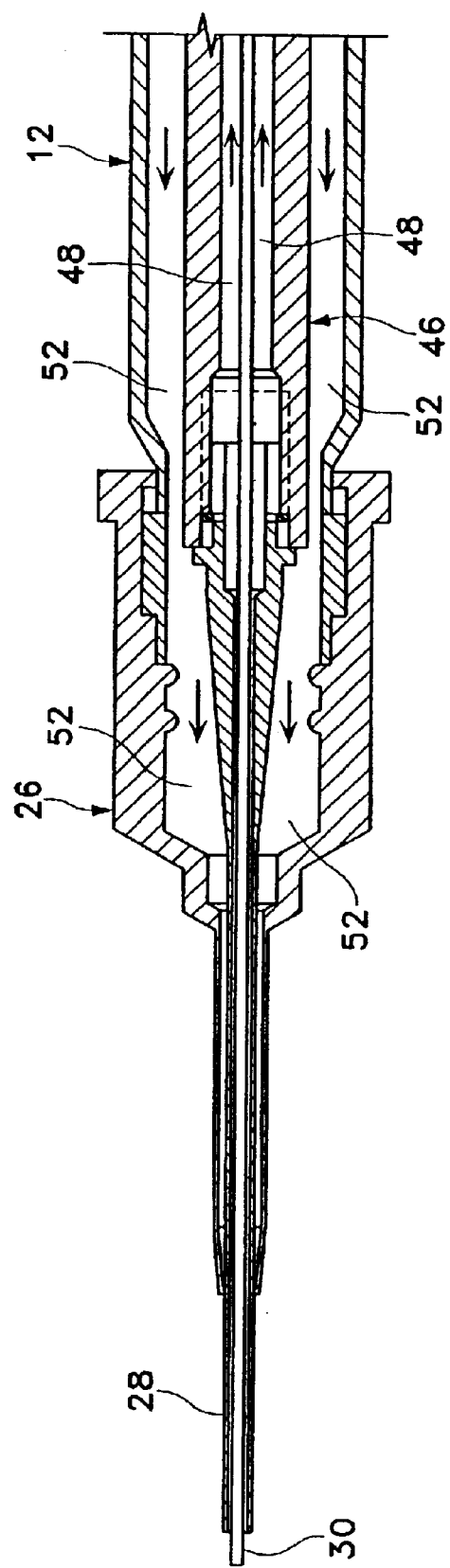
FIG. 6 is an enlarged partial cross-sectional view of the handpiece of FIG. 1 taken at circle 6 in FIG. 3.

Handpiece 10 of the present invention generally includes handpiece body 12 and operative tip 16. Body 12 generally includes external irrigation tube 18 and aspiration fitting 20. Body 12 is similar in construction to well-known in the art phacoemulsification handpieces and may be made from plastic, titanium or stainless steel. As best seen in FIG. 6, operative tip 16 includes tip/cap sleeve 26, needle 28 and tube 30. Sleeve 26 may be any suitable commercially available phacoemulsification tip/cap sleeve or sleeve 26 may be incorporated into other tubes as a multi-lumen tube. Needle 28 may be any commercially available hollow phacoemulsification cutting tip, such as the TURBOSONICS tip available from Alcon Laboratories, Inc., Fort Worth, Tex. Tube 30 may be any suitably sized tube to fit within needle 28, for example 29 gauge hypodermic needle tubing.

Figure 5:
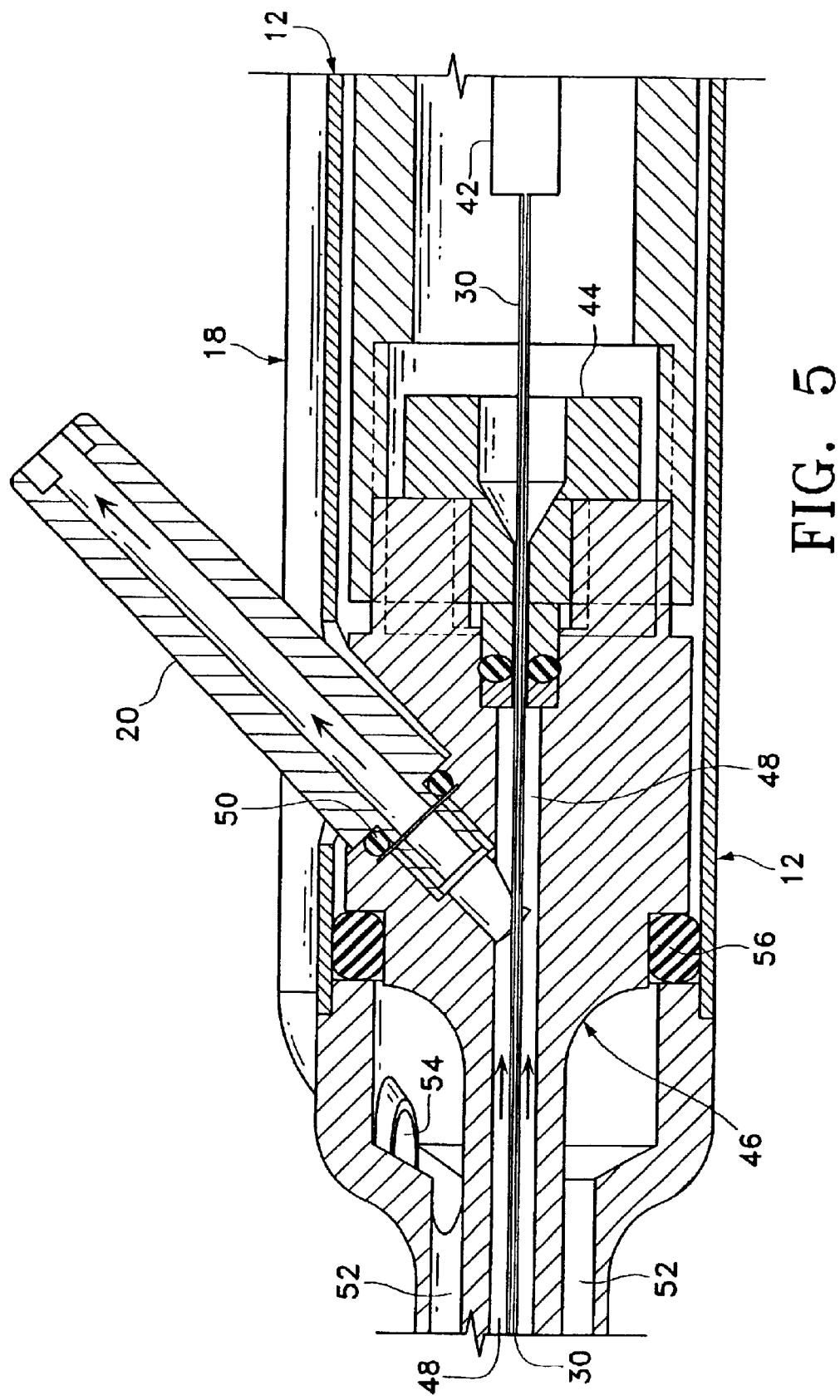
FIG. 5 is an enlarged partial cross-sectional view of the handpiece of FIG. 1 taken at circle 5 in FIG. 4.

As best seen in FIG. 5, tube 30 is free on the distal end and connected to pumping chamber 42 on the proximal end. Tube 30 and pumping chamber 42 may be sealed fluid tight by any suitable means having a relatively high melting point, such as a silicone gasket, glass frit or silver solder. Fitting 44 holds tube 30 within bore 48 of aspiration horn 46. Bore 48 communicates with fitting 20, which is journaled into horn 46 and sealed with O-ring seal 50 to form an aspiration pathway through horn 46 and out fitting 20. Horn 46 is held within body 12 by O-ring seal 56 to form irrigation tube 52 which communicates with irrigation tube 18 at port 54.

Figure 7:
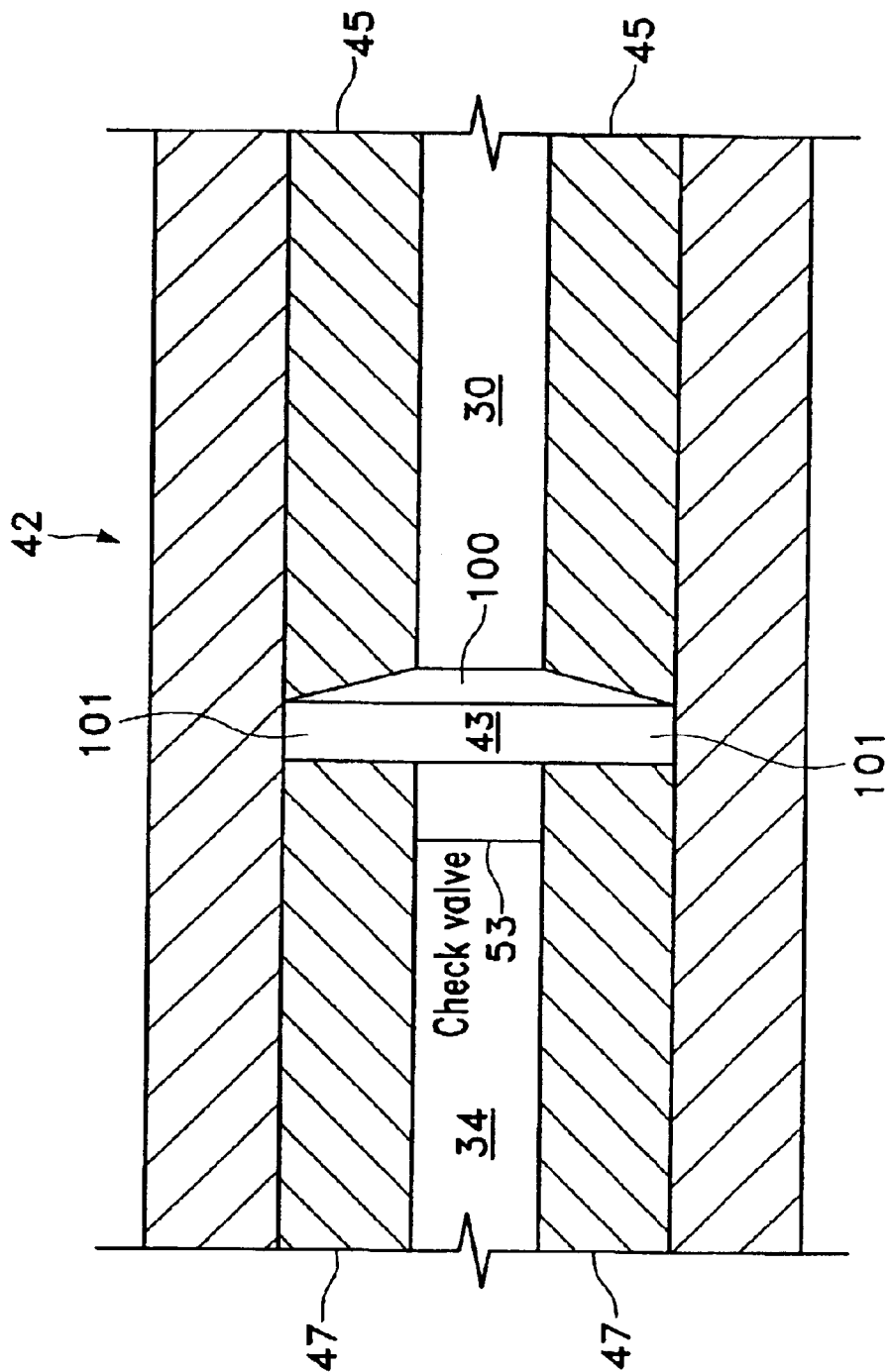
FIG. 7 is an enlarged cross-sectional view of the handpiece of FIG. 1 taken at circle 7 in FIGS. 3 and 4.

As best seen in FIG. 7, in a first embodiment of the present invention, pumping chamber 42 contains a relatively large pumping reservoir 43 that is sealed on both ends by electrodes 45 and 47. Electrical power is supplied to electrodes 45 and 47 by insulated wires, not shown. In use, surgical fluid (e.g. saline irrigating solution) enters reservoir 43 through port 55, tube 34 and check valve 53, check valves 53 being well-known in the art. Electrical current (preferably Radio Frequency Alternating Current or RFAC) is delivered to and across electrodes 45 and 47 because of the conductive nature of the surgical fluid. As the current flows through the surgical fluid, the surgical fluid boils. As the surgical fluid boils, it expands rapidly out of pumping chamber 42 through port 57 and into tube 30 (check valve 53 prevents the expanding fluid from entering tube 34). The expanding gas bubble pushes the surgical fluid in tube 30 downstream of pumping chamber 42 forward. Subsequent pulses of electrical current form sequential gas bubbles that move surgical fluid down tube 30. The size and pressure of the fluid pulse obtained by pumping chamber 42 can be varied by varying the length, timing and/or power of the electrical pulse sent to electrodes 45 and 47 and by varying the dimensions of reservoir 43. In addition, the surgical fluid may be preheated prior to entering pumping chamber 42. Preheating the surgical fluid will decrease the power required by pumping chamber 42 and/or increase the speed at which pressure pulses can be generated.

Figure 8:
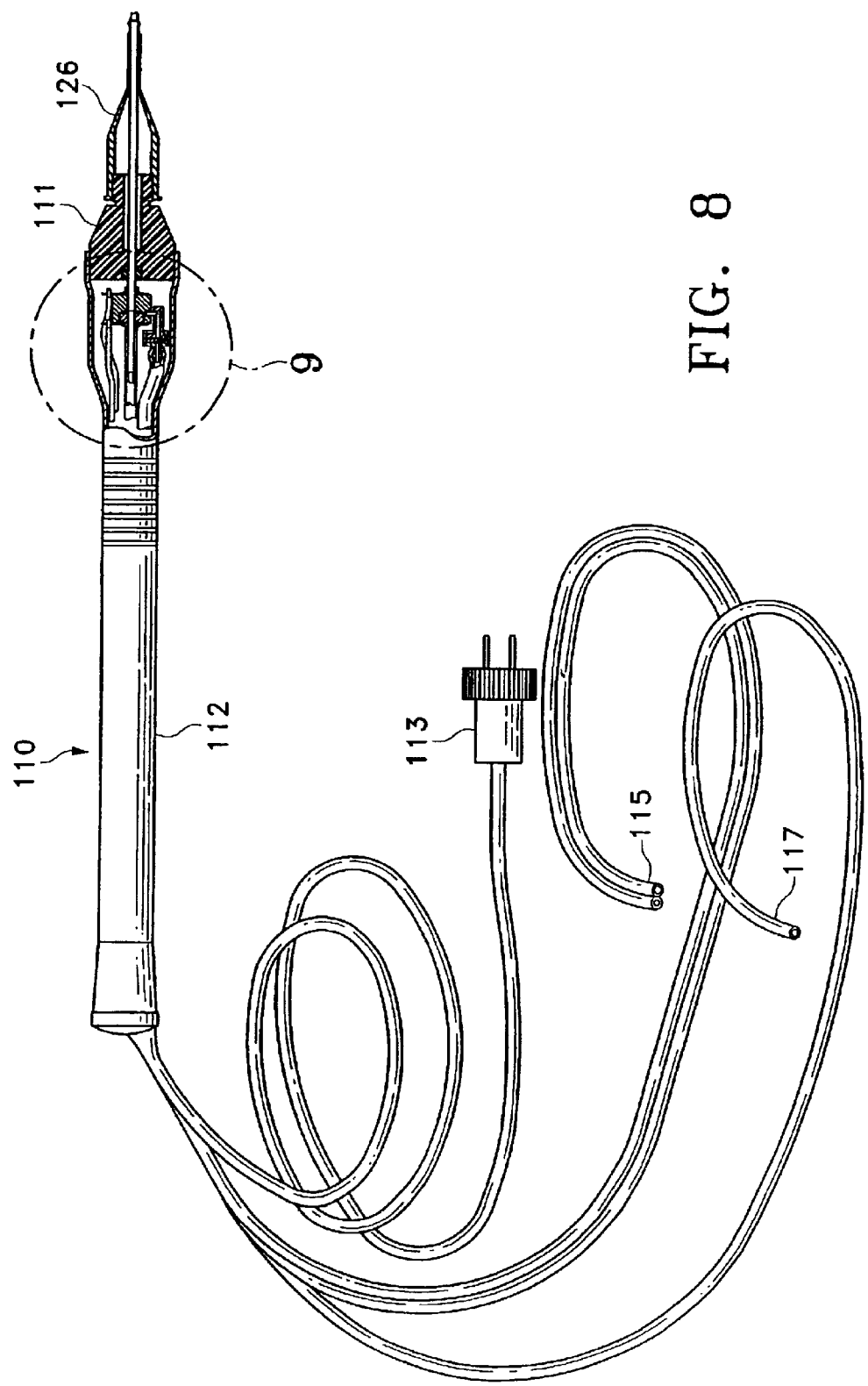
FIG. 8 is a partial cross-sectional view of a second preferred embodiment of the handpiece of the present invention.
Figure 9:
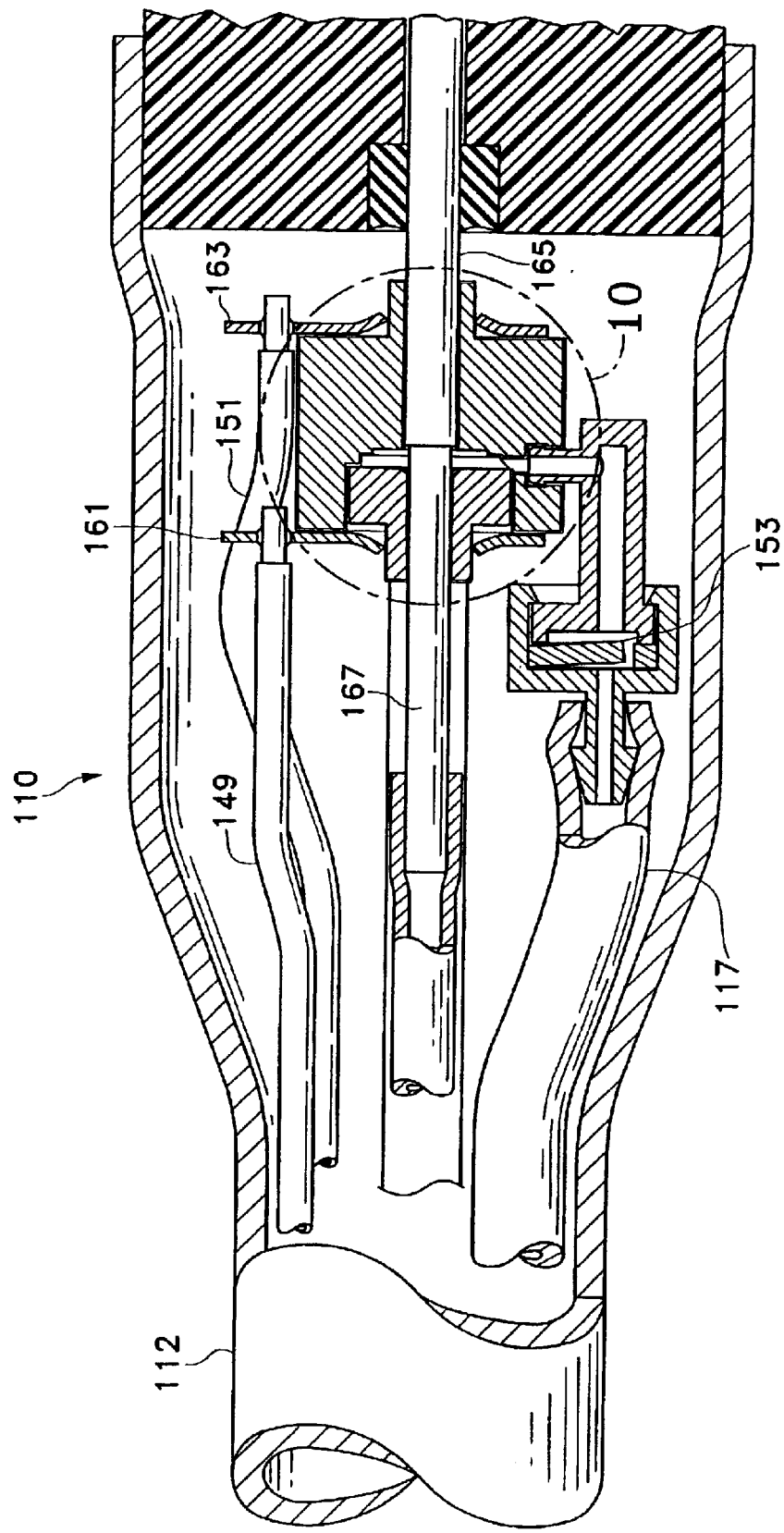
FIG. 9 is an enlarged partial cross-sectional view of the handpiece of FIG. 8 taken at circle 9 in FIG. 8.
Figure 10:
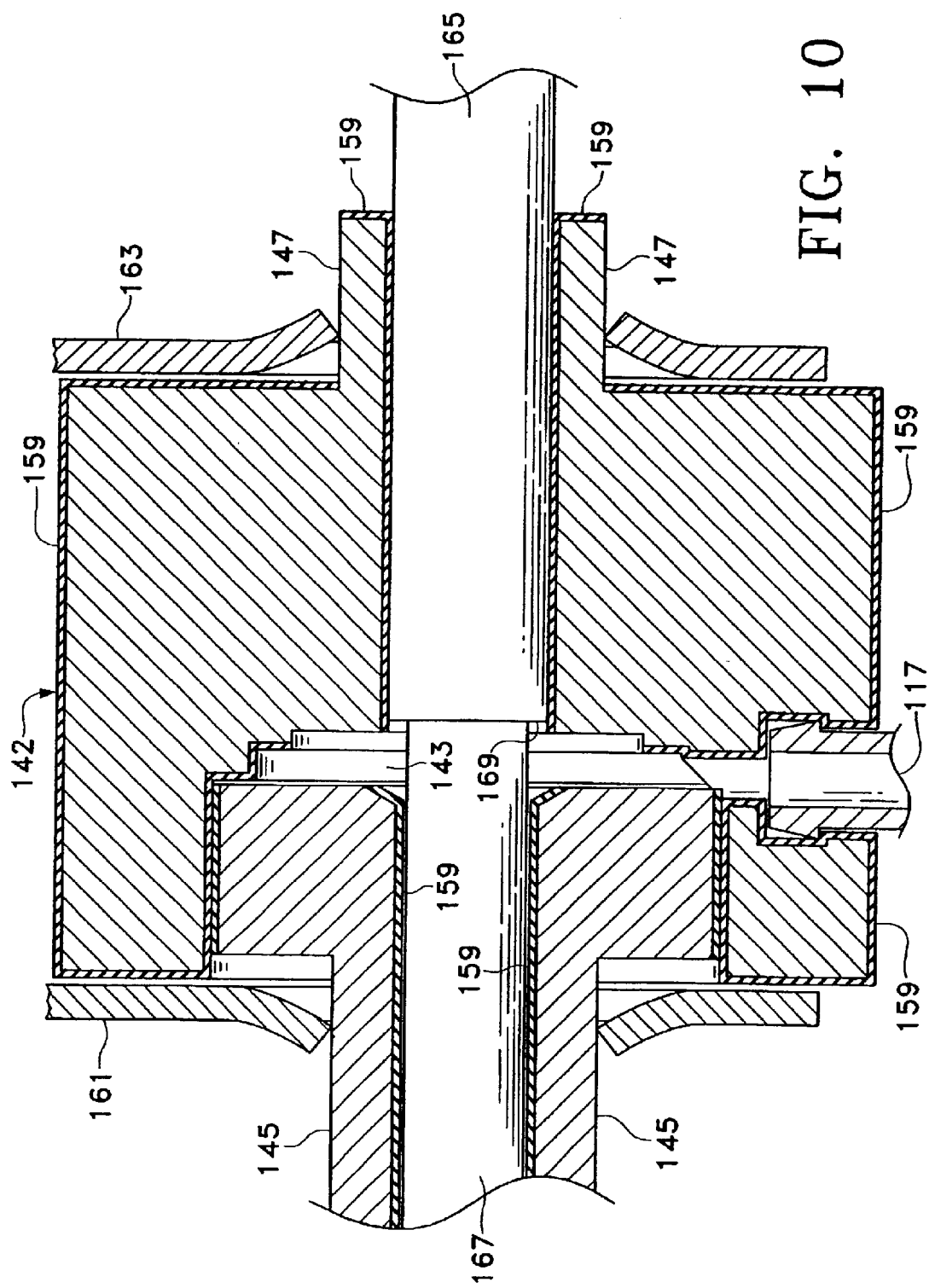
FIG. 10 is an enlarged partial cross-sectional view of the pumping chamber used in the handpiece of FIG. 8 taken at circle 10 in FIG. 9.

As best seen in FIGS. 8–10, in a second embodiment of the present invention, handpiece 110 generally includes body 112, having power supply cable 113, irrigation/ aspiration lines 115, and pumping chamber supply line 117. Distal end 111 of handpiece 110 contains pumping chamber 142 having a reservoir 143 formed between electrodes 145 and 147. Electrodes 145 and 147 are preferably made from aluminum, titanium, carbon or other similarly conductive materials and are electrically insulated from each other and body 112 by anodized layer 159 formed on electrodes 145 and 147. Anodized layer 159 is less conductive than untreated aluminum and thus, acts as an electrical insulator. Electrodes 145 and 147 and electrical terminals 161 and 163 are not anodized and thus, are electrically conductive. Layer 159 may be formed by any suitable anodization technique, well-known in the art, and electrodes 145 and 147 and electrical terminals 161 and 163 may be masked during anodization or machined after anodization to expose bare aluminum. Electrical power is supplied to electrodes 145 and 147 through terminals 161 and 163 and wires 149 and 151, respectively. Fluid is supplied to reservoir 143 though supply line 117 and check valve 153. Extending distally from pumping chamber 142 is outer tube 165 that coaxially surrounds aspiration tube 167. Tubes 165 and 167 may be of similar construction as tube 30. Tube 167 is of slightly smaller diameter than tube 165, thereby forming an annular passage or gap 169 between tube 165 and tube 167. Annular gap 169 fluidly communicates with reservoir 143.

In use, surgical fluid enters reservoir 143 through supply line 117 and check valve 153. Electrical current is delivered to and across electrodes 145 and 147 because of the conductive nature of the surgical fluid. As the current flows through the surgical fluid, the surgical fluid boils. As the surgical fluid boils, it expands rapidly out of pumping chamber 142 through annular gap 169. The expanding gas bubble pushes forward the surgical fluid in annular gap 169 downstream of pumping chamber 142. Subsequent pulses of electrical current form sequential gas bubbles that move or propel the surgical fluid down annular gap 169.

One skilled in the art will recognize that the numbering in FIGS. 8–10 is identical to the numbering in FIGS. 1–7 except for the addition of "100" in FIGS. 8–10.

Figure 11:
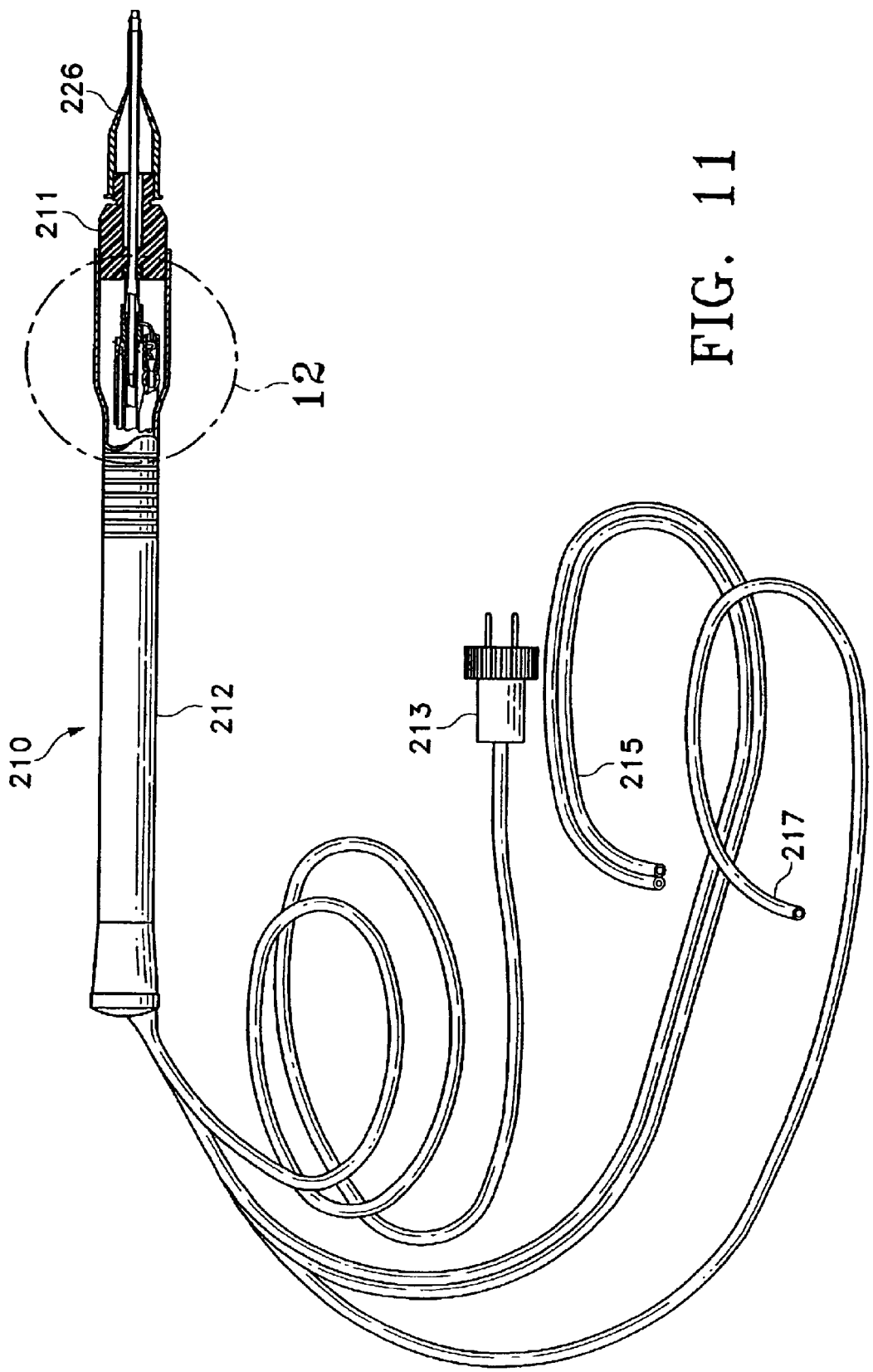
FIG. 11 is a partial cross-sectional view of a third preferred embodiment of the handpiece of the present invention.
Figure 12:
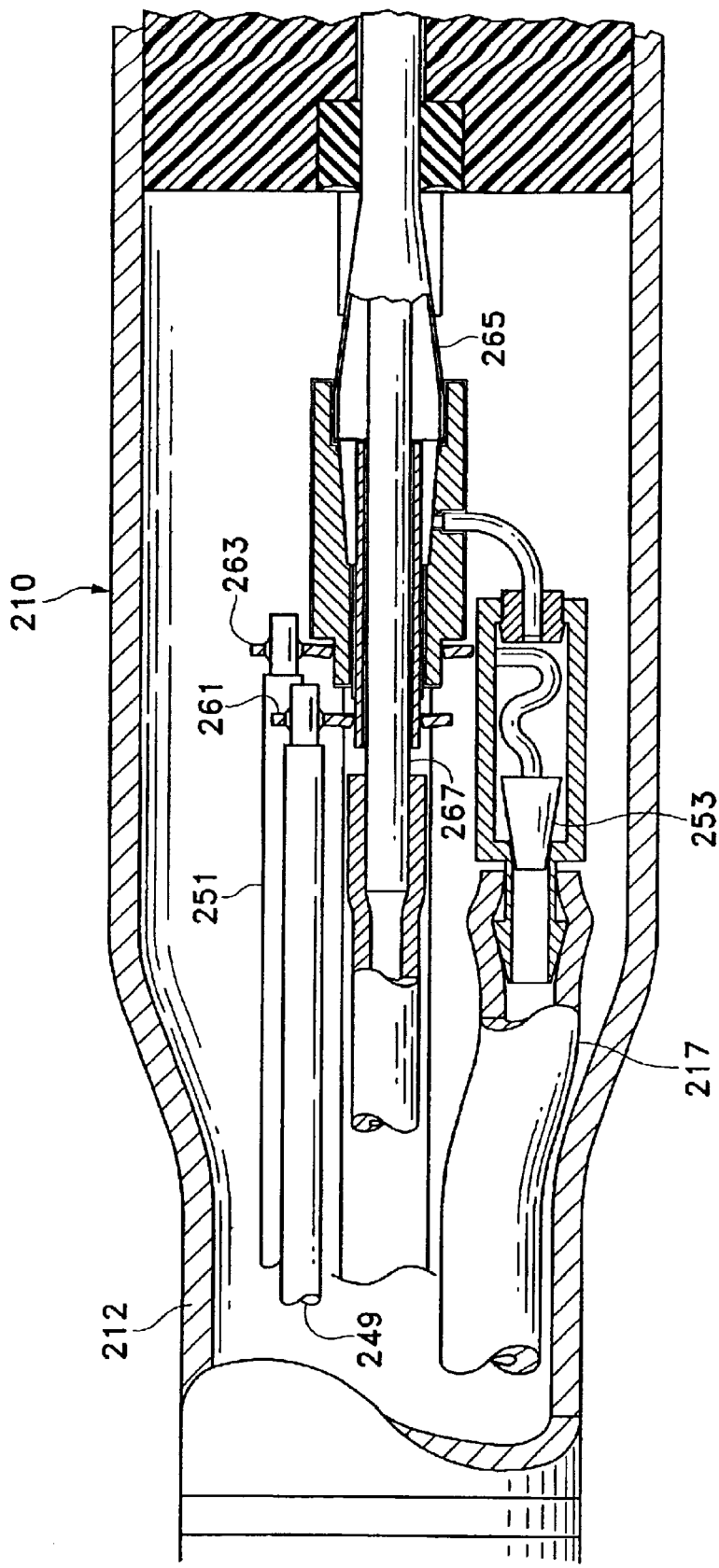
FIG. 12 is an enlarged partial cross-sectional view of the handpiece of FIG. 11 taken at circle 12 in FIG. 11.
Figure 13:
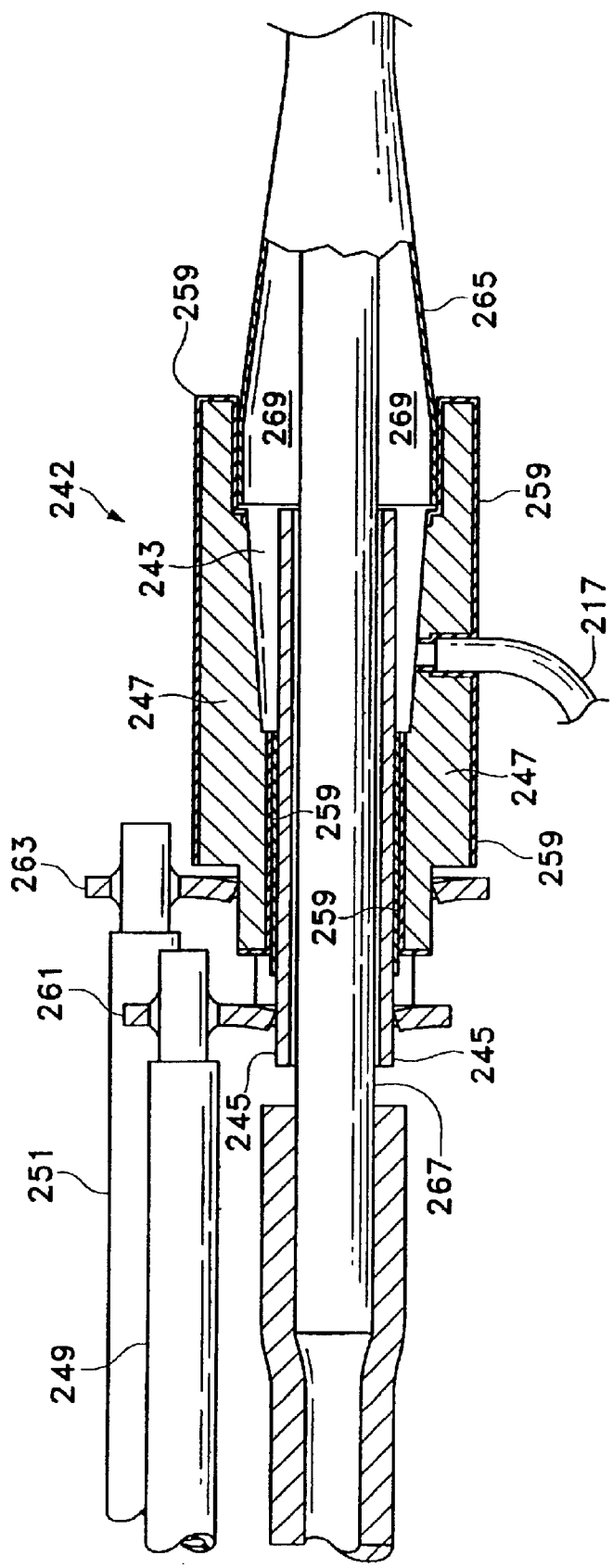
FIG. 13 is an enlarged partial cross-sectional view of the pumping chamber used in the handpiece of FIG. 11.
Figure 14:
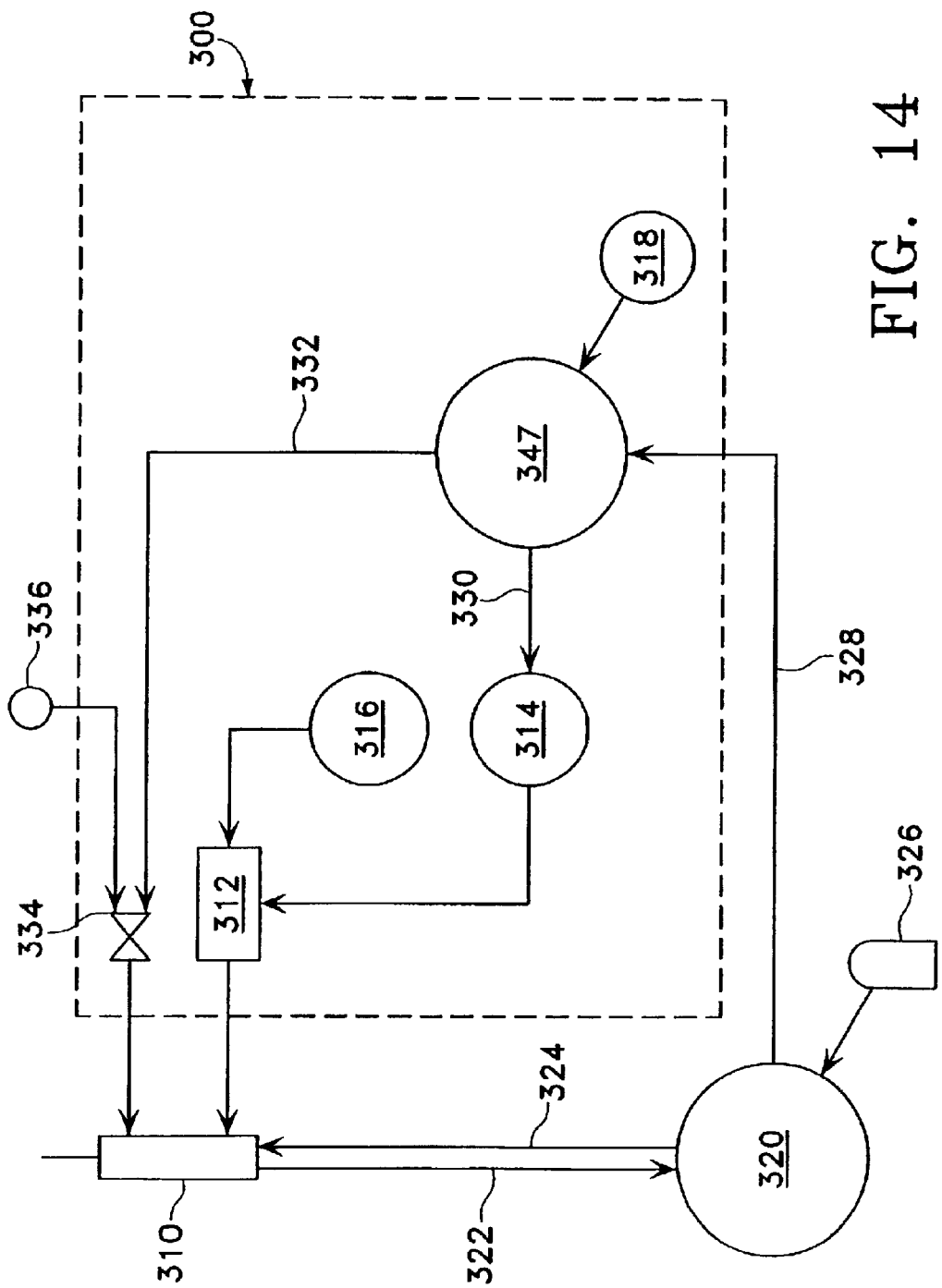
FIG. 14 is a block diagram of a control system that can be used with the handpiece of the present invention.
Figure 15:
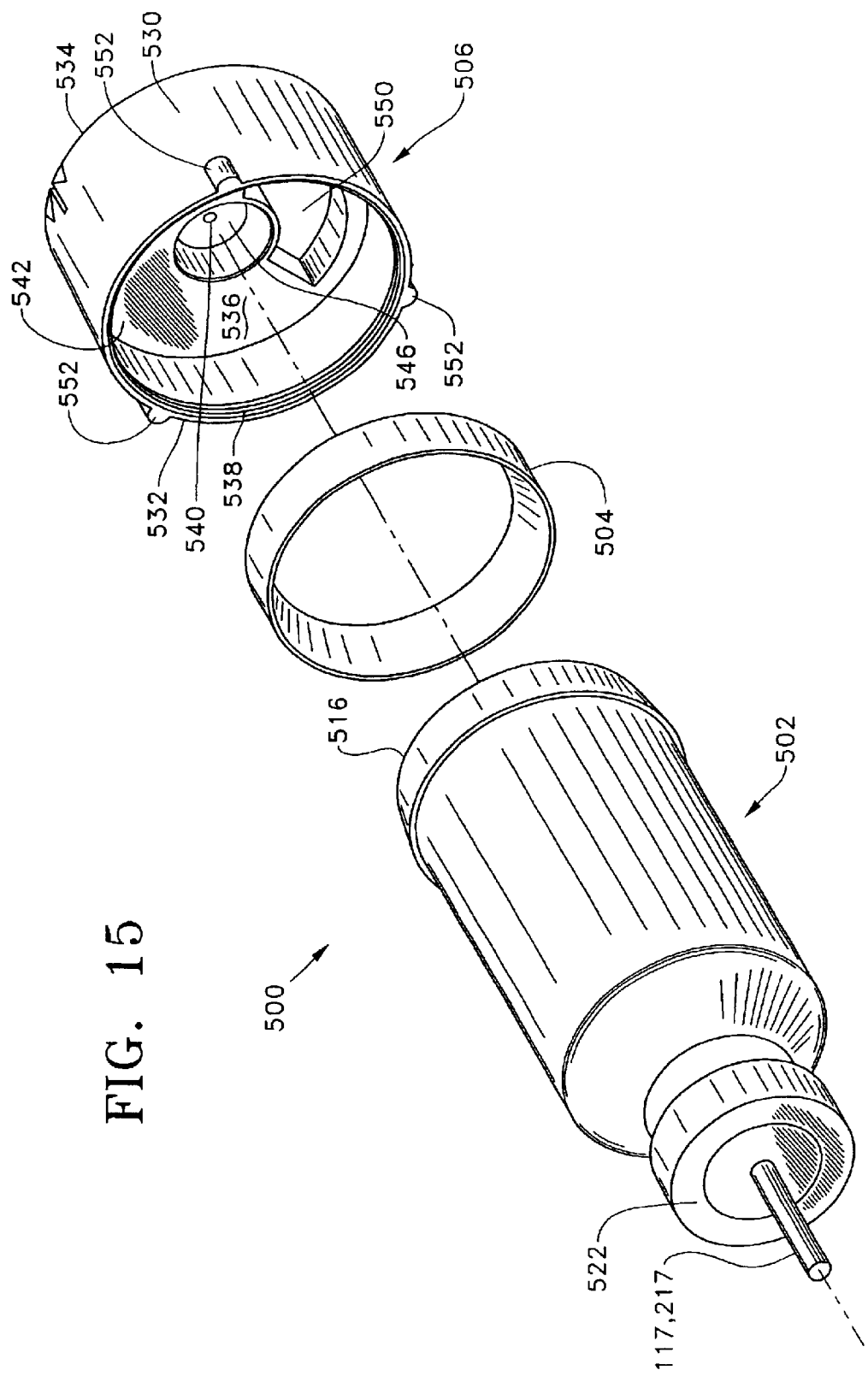
FIG. 15 is an exploded, front, right perspective view of an apparatus for the delivery of a surgical fluid to an ophthalmic surgical handpiece according to a preferred embodiment of the present invention.
Figure 19:
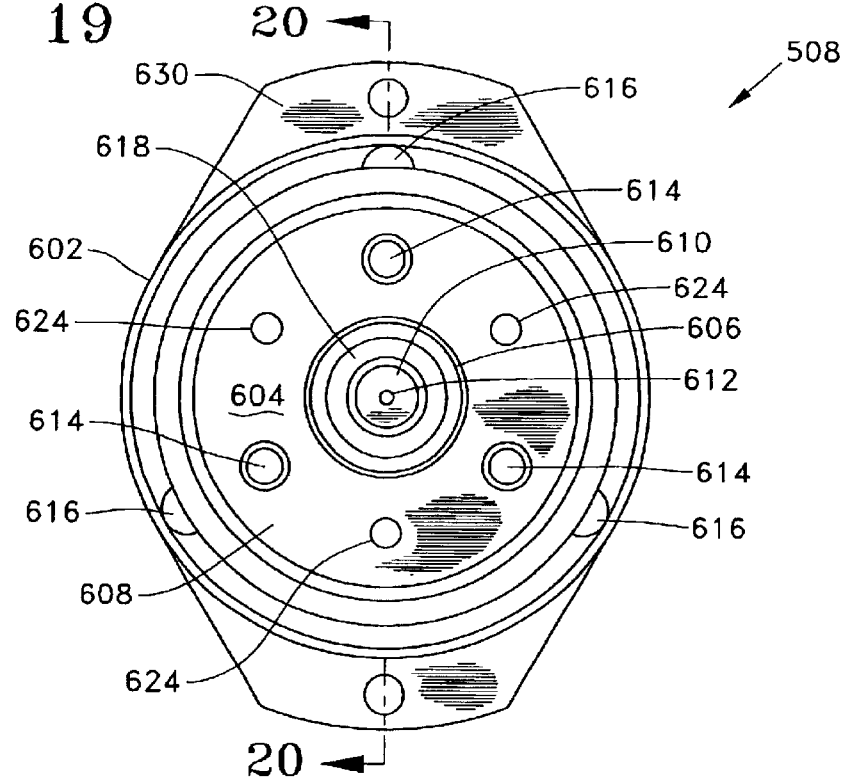
FIG. 19 is a front view of a preferred embodiment of a receptacle in a surgical console for receiving the apparatus of FIG. 15.
Figure 20:
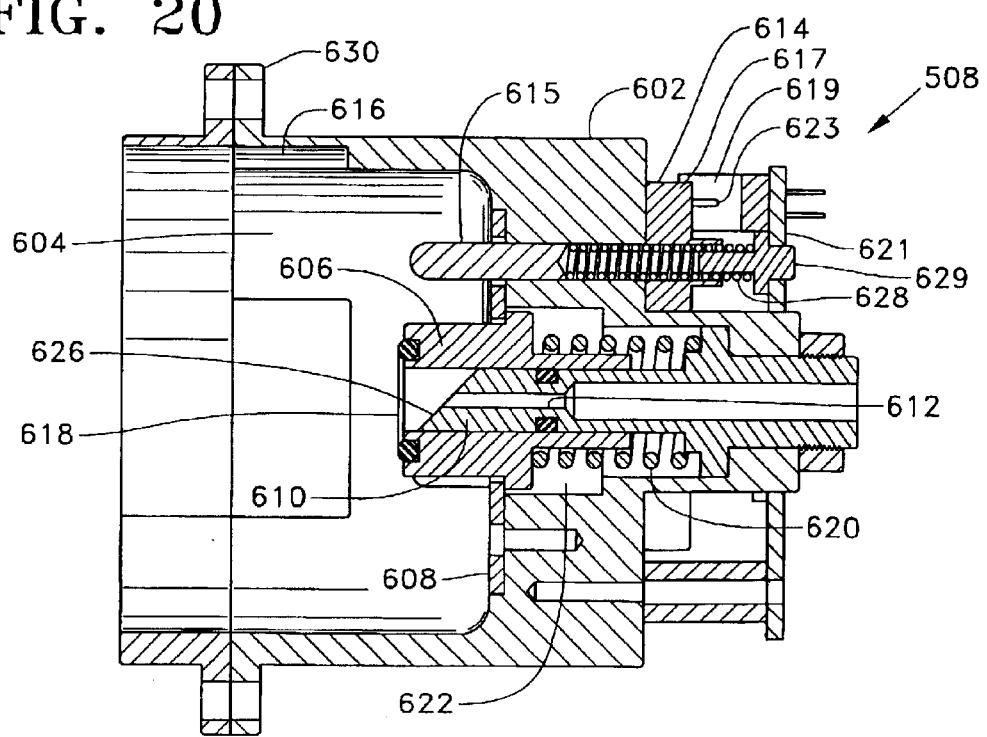
FIG. 20 is a side, sectional view of the receptacle of FIG. 19 along line 20—20.

As best seen in FIGS. 11–13, in a third embodiment of the present invention, handpiece 210 generally includes body 212, having power supply cable 213, irrigation/aspiration lines 215, and pumping chamber supply line 217. Distal end 211 of handpiece 210 contains pumping chamber 242 having a reservoir 243 formed between electrodes 245 and 247. Electrodes 245 and 247 are preferably made from aluminum and electrically insulated from each other and body 212 by anodized layer 259 formed on electrodes 245 and 247. Anodized layer 259 is less conductive than untreated aluminum and thus, acts as an electrical insulator. Electrodes 245 and 247 and electrical terminals 261 and 263 are not anodized and thus, are electrically conductive. Layer 259 may be formed by any suitable anodization technique, well-known in the art, and electrodes 245 and 247 and electrical terminals 261 and 263 may be masked during anodization or machined after anodization to expose bare aluminum. Electrical power is supplied to electrodes 245 and 247 through terminals 261 and 263 and wires 249 and 251, respectively. Fluid is supplied to reservoir 243 though supply line 217 and check valve 253. Extending distally from pumping chamber 242 is outer tube 265 that coaxially surrounds aspiration tube 267. Tubes 265 and 267 may be of similar construction as tube 30. Tube 267 is of slightly smaller diameter than tube 265, thereby forming an annular passage or gap 269 between tube 265 and tube 267. Annular gap 269 fluidly communicates with reservoir 243.

In use, surgical fluid enters reservoir 243 through supply line 217 and check valve 253. Electrical current is delivered to and across electrodes 245 and 247 because of the conductive nature of the surgical fluid. As the current flows through the surgical fluid, the surgical fluid boils. The current flow progresses from the smaller electrode gap section to the larger electrode gap section, i.e., from the region of lowest electrical resistance to the region of higher electrical resistance. The boiling wavefront also progresses from the smaller to the larger end of electrode 247. As the surgical fluid boils, it expands rapidly out of pumping chamber 242 through annular gap 269. The expanding gas bubble pushes forward the surgical fluid in annular gap 269 downstream of pumping chamber 242. Subsequent pulses of electrical current form sequential gas bubbles that move or propel the surgical fluid down annular gap 269.

One skilled in the art will recognize that the numbering in FIGS. 11–13 is identical to the numbering in FIGS. 1–7 except for the addition of "200" in FIGS. 11–13.

While several embodiments of the handpiece of the present invention are disclosed, any handpiece producing adequate pressure pulse force, temperature, rise time and frequency may also be used. For example, any handpiece producing a pressure pulse force of between 0.02 grams and 20.0 grams, with a rise time of between 1 gram/sec and 20,000 grams/sec and a frequency of between 1 Hz and 200 Hz may be used, with between 10 Hz and 100 Hz being most preferred. The pressure pulse force and frequency will vary with the hardness of the material being removed. For example, the inventors have found that a lower frequency with a higher pulse force is most efficient at debulking and removing the relatively hard nuclear material, with a higher frequency and lower pulse force being useful in removing softer epinuclear and cortical material. Infusion pressure, aspiration flow rate and vacuum limit are similar to current phacoemulsification techniques.

As seen in FIG. 10, one embodiment of control system 300 for use in operating handpiece 310 includes control module 347, power gain RF amplifier 312 and function generator 314. Power is supplied to RF amplifier 312 by DC power supply 316, which preferably is an isolated DC power supply operating at several hundred volts, but typically ±200 volts. Control module 347 may be any suitable microprocessor, micro controller, computer or digital logic controller and may receive input from operator input device 318. Function generator 314 provides the electric wave form in kilohertz to amplifier 312 and. typically operates at around 450 KHz or above to help minimize corrosion.

In use, control module 347 receives input from surgical console 320. Console 320 may be any commercially available surgical control console such as the LEGACY® SERIES TWENTY THOUSAND® surgical system available from Alcon Laboratories, Inc., Fort Worth, Tex. Console 320 is connected to handpiece 310 through irrigation line 322 and aspiration line 324, and the flow through lines 322 and 324 is controlled by the user via footswitch 326. Irrigation and aspiration flow rate information in handpiece 310 is provided to control module 347 by console 320 via interface 328, which may be connected to the ultrasound handpiece control port on console 320 or to any other output port. Control module 347 uses footswitch 326 information provided by console 320 and operator input from input device 318 to generate two control signals 330 and 332. Signal 332 is used to operate pinch valve 334, which controls the surgical fluid flowing from fluid source 336 to handpiece 310. Fluid from fluid source 336 is heated in the manner described herein. Signal 330 is used to control function generator 314. Based on signal 330, function generator 314 provides a wave form at the operator selected frequency and amplitude determined by the position of footswitch 326 to RF amplifier 312 which is amplified to advance the powered wave form output to handpiece 310 to create heated, pressurized pulses of surgical fluid.

Any of a number of methods can be employed to limit the amount of heat introduced into the eye. For example, the pulse train duty cycle of the heated solution can be varied as a function of the pulse frequency so that the total amount of heated solution introduced into the eye does not vary with the pulse frequency. Alternatively, the aspiration flow rate can be varied as a function of pulse frequency so that as pulse frequency increases aspiration flow rate increases proportionally.

FIGS. 15–18 show a preferred embodiment of an apparatus 500 for delivery of a surgical fluid to an ophthalmic surgical handpiece. Apparatus 500 is described herein as delivering a surgical fluid to a liquefracture handpiece such as liquefracture handpieces 10, 110, 210, or 310. However, apparatus 500 may also be used with other surgical handpieces, such as those used in otic or nasal surgery.

Apparatus 500 preferably includes a container 502, an annular gasket 504, and an adapter 506. Container 502 holds the surgical fluid for the liquefracture handpiece and is represented by fluid source 336 in FIG. 14. Adapter 506, in cooperation with gasket 504, forms a fluid tight seal on bottom portion 516 of container 502 and functions to engage apparatus 500 with a receptacle 508 (FIGS. 19 and 20) of surgical console 320.

Container 502 is preferably a conventional multilayer plastic bottle having a first portion or body 510 and a second portion or deformable liner 512 located within first portion 510. Second portion 512 is preferably formed from a deformable plastic that is separable from first portion 510. By way of example, second portion 512 may be formed of nylon. As another example, second portion 512 may be formed of an inner layer of polypropylene coupled to an outer layer of ethylene vinyl oxide with an adhesive therebetween. First portion 510 is preferably formed from a more rigid plastic than used to form second portion 512. By way of example, first portion 510 may be formed of high density polyethylene. As another example, first portion 510 may be formed of polypropylene. Container 502 is preferably formed using a conventional extrusion blow molding process. A wide variety of multilayer bottles may be utilized for container 502. An exemplary bottle, and a manufacturing technique therefor, is disclosed in U.S. Pat. No. 6,083,450 (Safian) and is incorporated herein in its entirety by this reference. Alternatively, first portion 510 may be formed from stainless steel or other relatively rigid, non-plastic material, and second portion 512 may be formed from a deformable material other than plastic.

First portion 510 generally includes an open mouth 514, a bottom 516, and a side wall 518. Bottom 516 is formed with an aperture 520. A circumferential shoulder 521 is preferably formed near bottom 516. Container 502 preferably also has a cap 522 that may be secured to mouth 514. Cap 522 is preferably made of aluminum and is crimp sealed to mouth 514. Alternatively, cap 522 may be secured to mouth 514 by way of threads (not shown). Cap 522 preferably includes a rubber stopper 523 having a hole 524 therethrough designed to sealingly receive pumping chamber supply line 117 or 217. Alternatively, mouth 514 of first portion 510 may be sealed only by rubber stopper 523.

Adapter 506 generally includes an outer wall 530, a first open end 532, a second open end 534, and a transverse wall 536. Adapter 506 is preferably made from conventional plastic such as, by way of example, polypropylene. Alternatively, adapter 506 may be formed from stainless steel or other relatively rigid, non-plastic material. Open end 532 receives gasket 504 and bottom 516 of container 502. Second open end 534 is for engaging receptacle 508. Outer wall 530 preferably has a circumferential flange 538 on its inside surface that engages shoulder 521 of container 502 to secure adapter 506 to container 502. Transverse wall 536 includes an aperture 540 that is preferably disposed in the center of adapter 506. Transverse wall 536 includes a first side 542 on the side of first open end 532, and a second side 544 on the side of second open end 534. Gasket 504 preferably rests on a first side 542 of transverse wall 536 and forms a fluid tight seal with bottom 516. First side 540 also preferably includes a recessed volume 546. Second side 544 preferably includes an annular skirt 548 and at least one raised surface 550. As shown best in FIGS. 15 and 18, raised surface 550 preferably has an arc length of about 120 degrees. The second side 544 of transverse wall 536 creates a pattern that can be used to identify the particular kind of surgical fluid held within container 502, and also whether adapter 506 is engaged within receptacle 508. Although not shown in the FIGS., second side 544 may be formed with no raised surface 550 or with various combinations of multiple raised surfaces 550. For example, two raised surfaces 550 may form a continuous raised surface of 240 degrees. As another example, three raised surfaces 550 may form a continuous raised surface of 360 degrees. One skilled in the art will recognize that, given the 120 degree arc length of raised surface 550 and the possible angular positions around aperture 540, second side 544 of transverse wall 536 may be formed with seven unique patterns of raised surfaces. Each such pattern is representative of a binary signal (e.g. 001, 011, 101, 110, 010, 111, 000) where 1 indicates the presence of a raised surface and 0 indicates the absence of a raised surface. Of course, if a different arc length is used for each raised surface 550, second side 544 of transverse wall 536 may be formed with more or less than seven unique patterns of raised surfaces. Three lugs 552 are disposed on an outer surface of outer wall 530. Lugs 552 are preferably spaced at 115 degree intervals around aperture 540.

Receptacle 508 generally includes a housing 602, an interior 604, a piston 606, a piston retainer 608, a pressure spine or needle 610, and a plurality of sensors 614. Interior 604 receives second open end 534 of adapter 506. The inner surface of interior 604 has three slots 616 for operative engagement with lugs 552 of adapter 506. Each of slots 616 preferably has a "L"-shaped geometry, with one leg of the "L" extending in a clockwise direction along the circumference of the inner surface of interior 604 for a distance of less than 90 degrees. Piston 606 has a face seal 618 on a front end thereof, and is biased outwardly from interior 604 by a spring 620 disposed in cavity 622. Piston retainer 608 secures piston 606 within interior 604 and is secured to housing 602 via bolts 624. Pressure spine 610 has a sharp tip 626 and a lumen 612 that is fluidly coupled to a source of pressurized fluid (e.g. pressurized air) within surgical console 320. Sensors 614 are preferably spaced at 120 degree intervals around pressure spine 610 for operative engagement with raised surfaces 550 of adapter 506. Each sensor 614 preferably includes a plunger 615 that is capable of movement along the longitudinal axis of housing 602 and that is biased outwardly by a spring 628 mounted on a spring seat 629; a fin 617 coupled to plunger 615, and an optical sensor 619 mounted on a printed circuit board 621. An optical path or signal (e.g. beam of light) is formed across the width of sensor 614 via dual apertures 623 of optical sensor 619. An exemplary optical sensor 619 suitable for sensor 614 is the EESJ3G interruptive sensor available from Omron Sensors. Alternatively, sensor 614 may be a conventional force resistive sensor that measures the deflection or deflection force of plunger 615. Such a force resistive sensor may be formed without fin 617, optical sensor 619, and printed circuit board 621. Receptacle 508 is mounted within surgical console 320 via mounting bracket 630.

When a user aligns lugs 552 with slots 616, slides second open end 534 of adapter 506 into interior 604, and then twists adapter 506 in a clockwise direction, adapter 506 is removably secured within receptacle 508. At the same time, the inner surface of annular skirt 548 engages the outer surface of piston 606, and piston 606 moves inwardly through cavity 622 allowing pressure spine 610 to engage aperture 540 of transverse wall 536. Recessed volume 546 prevents pressure spine 610 from contacting bottom 516 of container 502 or piercing second portion 512 holding the surgical fluid. At portions of second side 544 of transverse wall 536 containing raised surfaces 550, the plunger 615 of the corresponding sensor 614 is depressed. If no raised surface 550 is present, the plunger 615 of the corresponding sensor 614 is not depressed, or alternatively is depressed a smaller amount than when a raised surface 550 is present. When a plunger 615 of a sensor 614 is depressed, fin 617 moves between dual apertures 623 of optical sensor 619 to break the optical path of sensor 619. Each sensor 614 having a plunger 615 that is depressed combines to generate a binary, electrical signal representative of a unique pattern of raised surfaces 550 on second side 544 of transverse wall 536 that is transmitted to surgical console 320 via printed circuit board 621. Control module 347 of surgical console 320 may be programmed to associate such electrical signals with a particular surgical fluid having particular properties (e.g. viscosity, surgical fluid supply pressure). In addition, control module 347 may automatically alter or adjust surgical fluid supply pressure, or other operating parameters of control system 300, surgical console 320, or liquefracture handpiece 10, 110, 210, or 310, as a function of the particular surgical fluid.

Once apparatus 500 is engaged within receptacle 508 as described above, surgical fluid from container 502 is delivered to liquefracture handpiece 210 in the following preferred manner. Pressurized air is delivered from lumen 612 of pressure spine 610, through aperture 540 of adapter 506, and through aperture 520 of first portion 510 of container 502. As shown best in FIG. 21, the pressurized air enters the space between the outer surface of second portion 512 and the inner surface of first portion 510, separating second portion 512 from first portion 510, and at least partially collapsing second portion 512. The pressurized air forces the surgical fluid from within second portion 512 to handpiece 210 via tubing 217.

From the above, it may be appreciated that the present invention provides a simple and reliable apparatus and method of delivering a surgical fluid to a surgical handpiece. The invention further provides an automated way of identifying the particular surgical fluid to be provided to the handpiece.

The present invention is illustrated herein by example, and various modifications may be made by a person of ordinary skill in the art. For example, second transverse wall 536 of container 500, or second side 706 of transverse wall 702 of container 700, may be formed without aperture 540. In this case, reference numeral 540 indicates the longitudinal axis of container 500, and sharp tip 626 of pressure spine 610 may be formed to pierce second transverse wall 536 or transverse wall 702.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An apparatus for delivery of a surgical fluid to a surgical handpiece, comprising:
   a container having first and second portions, said first portion made from a deformable material and having a closed end, an open end, an outer surface, and a first volume for receiving a surgical fluid for delivery to a surgical handpiece, said second portion made from a material more rigid than said deformable material and having a first end, a second end, an outer surface, an inner surface, and a second volume receiving said first portion, said first end having an outlet for delivery of said surgical fluid, said second end having an aperture for receiving a pressurized fluid between said outer surface of said first portion and said inner surface of said second portion; and
   an adapter having an outer wall, a first open end, a second open end, and a transverse wall coupled to said outer wall and having first and second sides, said first end of said adapter receiving said second end of said second portion, said second side of said transverse wall having an area for removably engaging a source of said pressurized fluid so that said source of said pressurized fluid is in fluid communication with said aperture, and said second side of said transverse wall having a geometry for providing a binary signal indicative of a particular kind of said surgical fluid.

2. The apparatus of claim 1 wherein said area of said second side of said transverse wall is capable of being engaged by a lumen for providing said pressurized fluid.

3. The apparatus of claim 1 wherein said geometry comprises at least one raised surface.

4. The apparatus of claim 3 wherein said at least one raised surface has an arc length.

5. The apparatus of claim 3 wherein said geometry comprises a pattern of raised surfaces.

6. The apparatus of claim 5 wherein each of said raised surfaces has an arc length.

7. The apparatus of claim 1 wherein said first side of said transverse wall is sealingly engaged with said second end of said second portion.

8. The apparatus of claim 7 further comprising a gasket, and wherein said gasket is disposed between said second end of said second portion and said first side of said transverse wall.

9. The apparatus of claim 1 wherein said first portion is at least partially separable from said second portion when said surgical fluid is discharged from said first volume.

10. The apparatus of claim 1 further comprising:
    a stopper disposed in said outlet of said second portion; and
    tubing sealingly disposed within said stopper and in fluid communication with said first volume.

11. The apparatus of claim 1 wherein said outer wall of said adapter has a plurality of lugs for alignment and operative engagement with a receptacle in a surgical console.

12. The apparatus of claim 1 wherein said first side of said transverse wall defines a third volume between said transverse wall and said second end of said second portion, so that said source of said pressurized fluid is in fluid communication with said third volume.

13. A system for delivering a surgical fluid to a liquefracture handpiece, comprising:

a liquefracture handpiece having a pumping chamber;

a container having first and second portions, said first portion made from a deformable material and having a closed end, an open end, an outer surface, and a first volume for receiving a surgical fluid for delivery to a liquefracture handpiece, said second portion made from a material more rigid than said deformable material and having a first end, a second end, an outer surface, an inner surface, and a second volume receiving said first portion, said first end having an outlet for delivery of said surgical fluid, said second end having an aperture for receiving a pressurized fluid between said outer surface of said first portion and said inner surface of said second portion; and an adapter having an outer wall, a first open end, a second open end, and a transverse wall coupled to said outer wall and having first and second sides, said first end of said adapter receiving said second end of said second portion, said second side of said transverse wall having an area for removably engaging a source of said pressurized fluid so that said source of said pressurized fluid is in fluid communication with said aperture;

a surgical console containing said source of said pressurized fluid and having a receptacle for removably receiving said adapter, said receptacle having a lumen for fluidly coupling said source of said pressurized fluid with said area of said second side of said transverse wall; and tubing fluidly coupling said outlet of said second portion with said liquefracture handpiece;

whereby when said surgical console provides said pressurized fluid from said lumen, said pressurized fluid flows through said aperture and between said outer surface of said first portion and said inner surface of said second portion, and said surgical fluid is delivered to said pumping chamber by said tubing.

14. The system of claim 13 wherein said pressurized fluid is air.

15. The system of claim 13 wherein said second side of said transverse wall has a geometry for providing a binary signal indicative of a particular kind of said surgical fluid.

16. The system of claim 15 wherein said geometry comprises at least one raised surface.

17. The system of claim 15 wherein said receptacle comprises a plurality of sensors for operatively engaging said geometry for providing a binary signal indicative of a particular kind of said surgical fluid.

18. The system of claim 13 wherein said first side of said transverse wall is sealingly engaged with said second end of said second portion.

19. The system of claim 18 further comprising a gasket, and wherein said gasket is disposed between said second end of said second portion and said first side of said transverse wall.

20. The system of claim 13 wherein said outer wall of said adapter has a plurality of lugs for alignment and operative engagement with a plurality of slots in said receptacle.

21. The system of claim 20 wherein said lugs and slots cooperate to removably secure said adapter to said receptacle.

22. An apparatus for delivery of a surgical fluid to a surgical handpiece, comprising:

a container having first and second portions, said first portion made from a deformable material and having a closed end, an open end, an outer surface, and a first volume for receiving a surgical fluid for delivery to a surgical handpiece, said second portion made from a material more rigid than said deformable material and having a first end, a second end, an outer surface, an inner surface, and a second volume receiving said first portion, said first end having an outlet for delivery of said surgical fluid, said second end having an aperture for receiving a pressurized fluid between said outer surface of said first portion and said inner surface of said second portion; and an adapter having an outer wall, a first open end, a second open end, and a transverse wall coupled to said outer wall and having first and second sides, said first end of said adapter receiving said second end of said second portion, said second side of said transverse wall having an area for removably engaging a source of said pressurized fluid so that said source of said pressurized fluid is in fluid communication with said aperture, and said outer wall of said adapter having a plurality of lugs for alignment and operative engagement with a receptacle in a surgical console.

23. An apparatus for delivery of a surgical fluid to a surgical handpiece, comprising:

a container having first and second portions, said first portion made from a deformable material and having a closed end, an open end, an outer surface, and a first volume for receiving a surgical fluid for delivery to a surgical handpiece, said second portion made from a material more rigid than said deformable material and having a first end, a second end, an outer surface, an inner surface, and a second volume receiving said first portion, said first end having an outlet for delivery of said surgical fluid, said second end having an aperture for receiving a pressurized fluid between said outer surface of said first portion and said inner surface of said second portion; and an adapter having an outer wall, a first open end, a second open end, and a transverse wall coupled to said outer wall and having first and second sides, said first end of said adapter receiving said second end of said second portion, said second side of said transverse wall having an area for removably engaging a source of said pressurized fluid so that said source of said pressurized fluid is in fluid communication with said aperture, and said first side of said transverse wall defining a third volume between said transverse wall and said second end of said second portion, so that said source of said pressurized fluid is in fluid communication with said third volume.

* * * * *